US009687141B2

(12) United States Patent
McGrath

(10) Patent No.: US 9,687,141 B2
(45) Date of Patent: Jun. 27, 2017

(54) LARYNGOSCOPE WITH MEANS TO RESTRICT RE-USE OF BLADES

(75) Inventor: Matthew J. R. McGrath, Edinburgh (GB)

(73) Assignee: AIRCRAFT MEDICAL LIMITED, Edinburgh (DE)

( * ) Notice: Subject to any disclaimer, the term of this patent is extended or adjusted under 35 U.S.C. 154(b) by 601 days.

(21) Appl. No.: 10/554,730

(22) PCT Filed: Apr. 29, 2004

(86) PCT No.: PCT/GB2004/001844
§ 371 (c)(1),
(2), (4) Date: Dec. 28, 2006

(87) PCT Pub. No.: WO2004/096031
PCT Pub. Date: Nov. 11, 2004

(65) Prior Publication Data
US 2007/0299313 A1    Dec. 27, 2007

(30) Foreign Application Priority Data
Apr. 29, 2003    (GB) .................................. 0309754.0

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00016* (2013.01); *A61B 1/00052* (2013.01); *A61B 1/00087* (2013.01); *A61B 1/00101* (2013.01); *A61B 1/04* (2013.01); *A61B 1/0661* (2013.01); *A61M 16/0488* (2013.01); *A61N 5/1043* (2013.01); *A61B 1/00029* (2013.01);
(Continued)

(58) Field of Classification Search
USPC ........................... 600/184–246; 604/131–132
See application file for complete search history.

(56) References Cited

U.S. PATENT DOCUMENTS

| 3,643,654 A | 2/1972 | Felbarg |
| 4,086,919 A | 5/1978 | Bullard |

(Continued)

FOREIGN PATENT DOCUMENTS

| EP | 0653180 B1 | 10/1998 |
| EP | 0901772 A1 | 3/1999 |

(Continued)

OTHER PUBLICATIONS

Woodson, "Retropalatal Airway Characteristics in Uvulopalatopharyngoplasty Compared With Transpalatal Advacement Pharyngoplasty"; Laryngoscope 107, Jun. 1997, pp. 735-740.
(Continued)

*Primary Examiner* — Matthew Lawson
(74) *Attorney, Agent, or Firm* — Fletcher Yoder PC

(57) ABSTRACT

A medical device for carrying out internal examination, such as laryngoscopes, has a body including a transmitter and receiver, and a blade portion including a receiver and transmitter. The transmitters and receivers are used to provide an indication of whether or not a particular blade portion has already been attached to a body portion previously.

9 Claims, 2 Drawing Sheets

(51) Int. Cl.
*A61N 5/10* (2006.01)
*A61B 1/04* (2006.01)
*A61B 1/06* (2006.01)
*A61M 16/04* (2006.01)
*A61B 90/00* (2016.01)

(52) U.S. Cl.
CPC ....... *A61B 1/00059* (2013.01); *A61B 1/00062* (2013.01); *A61B 2090/0803* (2016.02); *A61B 2090/0814* (2016.02); *A61B 2560/0276* (2013.01)

(56) References Cited

U.S. PATENT DOCUMENTS

| | | | |
|---|---|---|---|
| 4,113,137 A | 9/1978 | Wind | |
| 4,126,127 A * | 11/1978 | May | 600/187 |
| 4,306,547 A | 12/1981 | Lowell | |
| 4,384,570 A | 5/1983 | Roberts | |
| 4,406,280 A * | 9/1983 | Upsher | 600/193 |
| 4,556,052 A | 12/1985 | Muller | |
| 4,573,451 A | 3/1986 | Bauman | |
| 4,742,819 A | 5/1988 | George | |
| 4,832,003 A | 5/1989 | Yabe | |
| 4,832,020 A | 5/1989 | Augustine | |
| 4,930,495 A * | 6/1990 | Upsher | 600/193 |
| 4,934,773 A | 6/1990 | Becker | |
| 4,982,729 A | 1/1991 | Wu | |
| 5,003,963 A | 4/1991 | Bullard et al. | |
| 5,203,320 A | 4/1993 | Augustine | |
| 5,233,426 A | 8/1993 | Suzuki et al. | |
| 5,239,983 A | 8/1993 | Katsurada | |
| 5,261,392 A | 11/1993 | Wu | |
| 5,339,805 A | 8/1994 | Parker | |
| 5,349,943 A | 9/1994 | Ruiz | |
| 5,355,870 A * | 10/1994 | Lacy | 600/241 |
| 5,363,838 A | 11/1994 | George | |
| 5,373,317 A | 12/1994 | Salvati et al. | |
| 5,381,787 A | 1/1995 | Bullard | |
| D358,471 S | 5/1995 | Cope et al. | |
| 5,413,092 A | 5/1995 | Williams, III et al. | |
| 5,443,058 A | 8/1995 | Ough | |
| 5,513,627 A | 5/1996 | Flam | |
| 5,551,946 A * | 9/1996 | Bullard | 600/194 |
| 5,594,497 A | 1/1997 | Ahern et al. | |
| 5,645,519 A | 7/1997 | Lee et al. | |
| 5,676,635 A | 10/1997 | Levin | |
| 5,701,904 A | 12/1997 | Simmons et al. | |
| 5,702,351 A * | 12/1997 | Bar-Or et al. | 600/190 |
| 5,734,418 A | 3/1998 | Danna | |
| 5,734,718 A | 3/1998 | Prafullchandra | |
| 5,754,313 A | 5/1998 | Pelchy et al. | |
| 5,762,605 A | 6/1998 | Cane et al. | |
| 5,800,342 A | 9/1998 | Lee et al. | |
| 5,800,344 A | 9/1998 | Wood, Sr. et al. | |
| 5,827,178 A * | 10/1998 | Berall | 600/185 |
| 5,827,428 A | 10/1998 | Chang | |
| 5,846,186 A | 12/1998 | Upsher | |
| 5,873,818 A | 2/1999 | Rothfels | |
| 5,879,289 A | 3/1999 | Yarush et al. | |
| 5,879,304 A * | 3/1999 | Shuchman et al. | 600/193 |
| 5,895,350 A | 4/1999 | Hori | |
| 6,056,716 A * | 5/2000 | D'Antonio et al. | 604/68 |
| 6,080,101 A | 6/2000 | Tatsuno et al. | |
| 6,095,972 A | 8/2000 | Sakamoto | |
| 6,354,993 B1 | 3/2002 | Kaplan et al. | |
| 6,543,447 B2 | 4/2003 | Pacey | |
| 6,676,598 B2 * | 1/2004 | Rudischhauser et al. | 600/188 |
| 6,826,422 B1 * | 11/2004 | Modell et al. | 600/407 |
| 6,847,490 B1 | 1/2005 | Nordstrom et al. | |
| 6,964,637 B2 * | 11/2005 | Dalle et al. | 600/193 |
| 7,001,330 B2 * | 2/2006 | Kobayashi | 600/118 |
| 7,001,366 B2 * | 2/2006 | Ballard | 604/317 |
| 7,128,710 B1 * | 10/2006 | Cranton et al. | 600/199 |
| 7,156,091 B2 | 1/2007 | Koyama et al. | |
| 7,182,728 B2 | 2/2007 | Cubb et al. | |
| 7,214,184 B2 * | 5/2007 | McMorrow | 600/185 |
| 7,448,377 B2 | 11/2008 | Koyama et al. | |
| 2001/0051766 A1 * | 12/2001 | Gazdzinski | 600/309 |
| 2002/0022769 A1 * | 2/2002 | Smith et al. | 600/188 |
| 2002/0038076 A1 * | 3/2002 | Sheehan et al. | 600/200 |
| 2002/0087050 A1 * | 7/2002 | Rudischhauser et al. | 600/199 |
| 2002/0107436 A1 * | 8/2002 | Barton et al. | 600/382 |
| 2002/0198554 A1 | 12/2002 | Whitman et al. | |
| 2003/0195390 A1 * | 10/2003 | Graumann | 600/188 |
| 2004/0015132 A1 * | 1/2004 | Brown | 604/131 |
| 2004/0127770 A1 | 7/2004 | McGrath | |
| 2005/0090712 A1 | 4/2005 | Cubb | |
| 2006/0129031 A1 * | 6/2006 | Roberts et al. | 600/131 |
| 2006/0276694 A1 | 12/2006 | Acha Gandarias | |

FOREIGN PATENT DOCUMENTS

| | | |
|---|---|---|
| EP | 1188420 A1 | 3/2002 |
| EP | 1 285 623 A1 | 2/2003 |
| EP | 1285623 A1 | 2/2003 |
| FR | 2830428 A1 | 4/2003 |
| GB | 2 086 732 A | 5/1982 |
| JP | 61141342 | 6/1986 |
| JP | 2000175867 A | 6/2000 |
| WO | 83/01373 A1 | 4/1983 |
| WO | WO-89/11305 A1 | 11/1989 |
| WO | WO-91/04703 | 4/1991 |
| WO | WO-95/13023 | 5/1995 |
| WO | WO-98/19589 | 5/1998 |
| WO | WO-9841137 A1 | 9/1998 |
| WO | WO-99/27840 A1 | 6/1999 |
| WO | WO-99/44490 | 9/1999 |
| WO | WO-00/74556 A2 | 12/2000 |
| WO | WO-01/10293 A1 | 2/2001 |
| WO | WO-01/78582 A1 | 10/2001 |
| WO | WO-0178582 A1 | 10/2001 |
| WO | WO-0211608 A2 | 2/2002 |
| WO | WO-02/056756 A2 | 7/2002 |
| WO | WO-02/095675 A1 | 11/2002 |
| WO | WO-03/015619 A1 | 2/2003 |
| WO | WO-03/077738 A1 | 9/2003 |
| WO | WO-03/077738 A1 | 9/2003 |

OTHER PUBLICATIONS

Satava, "A technologic framework for the future"; Surgical Endoscopy (1993) 7: 111-113.

Meinke, et al, "What is the learning curve for laparoscopic appendectomy?"; Surgical Endoscopy (1994) 8: 371-375.

Cunningham, "Laparpscopic surgery—anesthetic implications"; Surgical Endoscopy (1994) 8: 1272-1284.

Siker ES, "A Mirror Laryngoscope", Anaesthesiology 17:38-42, 1956.

Australian Search Report.

International Search Report.

Murphy, et al. "Rigid and Semirigid Fiberoptic Intubation", Manual of Emergency Airway Management, The Airways, Lippincott Williams & Wilkins, 2004.

Crosby, et al., "The Unanticipated Difficult Airway With Recomendations for Management", Can J Anaesth 1998 pp. 757-776.

Biro, et al., "Comparison of Two Video-Assisted Techniques for the Difficult Intubation", 2001, pp. 761-765.

Bellhouse, et al., "An Angulated Laryngoscope for Routine and Difficult Trachael Intubation", 1997, pp. 126-129.

Pearce, et al., "Evaluation of the Upsherscope", 1996, pp. 561-564.

Smith, et al., The Complexity of Trachael Intubation Using Rigid Fiberoptic Laryngoscopy (WuScope), Anesth Analg, 1999, pp. 236-239.

Cooper, "Use of a New Videolaryngoscope (GlideScope®) in the Management of a Difficult Airway", Can J Anesth, 2003, pp. 611-613.

Dullenkopf, et al., "Video-enhanced Visualization of he Larynx and intubation with teh Bullard Laryngoscope—equipment report" Can J Anesth 2003, pp. 507-510.

(56) References Cited

OTHER PUBLICATIONS

Thompson, "A New Video Laryngoscope", Anaesthesia, 2004, pp. 410.
Esler, et al., "Decontaminationoflaryngoscopes: asurveyofnational Practice", Anaesthesia, 1999, pp. 582-598.
Morrell, et al., "A Survey of Laryngoscope Contamination at a University and a Community Hospital", Anesthesiology, 1994, pp. 960.
Weiss, M. "Video-intuboscopy: a new aid to routine and difficult tracheal intubation", British Journal of Anaesthesia 1998; 80: 525-527.
U.S. Appl. No. 60/067,205.
U.S. Appl. No. 60/074,355.
U.S. Appl. No. 09/060,891.
U.S. Appl. No. 60/223,330.
U.S. Appl. No. 09/732,129.

* cited by examiner

LARYNGOSCOPE WITH MEANS TO RESTRICT RE-USE OF BLADES

The present invention relates to medical devices for carrying out internal examination and relates particularly to laryngoscopes to assist intubation of a tracheal tube that have disposable sections.

Insertion of a tracheal tube is an important procedure in providing an airway to an anaesthetist prior to a surgical operation. Tracheal tubes also often need to be inserted in an emergency situation into the airway of an unconscious patient by paramedics or doctors. Insertion of a tracheal tube requires significant skill, and laryngoscopes are generally used to assist the insertion of the tube by restraining the patient's tongue and allowing a clear view of the larynx and the entrance to the trachea. Considerable skill and care is required in carrying out this procedure in order to avoid damage to the patient's teeth and soft tissue of the throat.

Often problems occur when a practitioner is attempting to intubate a patient using a laryngoscope as it is often difficult for the practitioner to see what is going on.

Figures show that in approximately 12% of cases trauma occurs during intubation (which affects a large number of people when you consider there are over 12 million intubations carried out annually).

A UK wide study found 50% of apparently clean laryngoscope handles waiting for re-use to be contaminated with blood from previous procedures. This is due to design flaws in the traditional laryngoscope and ineffective cleaning practice within hospitals. Where disposable single use surgical instruments have already been introduced, 12% of hospitals are actually re-using them due to the high cost of replacement. Making the situation worse, these elements are often never cleaned due to the assumption of single use sterility.

Obviously in order to use a laryngoscope on a patient, it is important to know that the laryngoscope is cleaned sufficiently and there is no risk of cross contamination between patients. There is evidence to show that standard cleaning procedures are not always fully effective at removing contaminants such as bacteria from the laryngoscope (J R Hall. 'Blood contamination of equipment . . .' Anaesthesia and Analgesia. 1994; 78:1136-9 M D Ester, L C Baines, D J Wilkinson & R M Langford. 'Decontamination of Laryngoscopes: a survey of national practice.' Anaesthesia, 1999, 54).

Typically, in order to clean a laryngoscope, the blade is soaked and autoclaved. The handle can undergo a similar procedure or can simply be wiped down as it does not make contact with the patient as the blade does. The cleaning takes a significant amount of time, which means that it is necessary to have a number of handles and blades in rotation to ensure that there are always clean laryngoscopes available if required. This results in a time consuming and costly procedure needing to be put in place.

In order to try and overcome the problems associated with laryngoscope disposable blades have been suggested for use. Unfortunately, it is common in practice that the blades are still used multiple times before being discarded. Flexible protective sheaths can also be used which slip over a standard laryngoscope blade to act as a guard. While useful, it is optional to a user whether the sheath is used or not. For the user, existing blades perform better without the sheath, which distorts light output and, as a result, existing sheaths are rarely used.

The present invention attempts to improve upon the prior art.

Throughout this Application the term blade should be read in a broad sense to cover not only laryngoscope blades but also to cover speculums or elements that are inserted into body cavities.

According to a first aspect of the present invention, there is provided a medical device comprising a body portion and a blade portion, wherein the blade portion is separable from the body portion characterised by the medical device being provided with spoiling means for indicating if a particular blade portion has already been attached to the body portion previously.

Optionally, the spoiling means will prevent reattachment of a blade that has already been attached to a body portion previously.

Preferably, the spoiling means comprises transmitting and receiving means in the body, which send and receive signals respectively with receiving and transmitting means in the blade.

Preferably the receiving means in the body can determine from the transmitting means in the blade, if the blade has previously been brought into close proximity of a body.

Preferably the transmitting means is a radio frequency transmitter.

Preferably the receiving means is a radio frequency receiver.

Optionally, the receiving means in the body will count the number of blades it contacts in its life.

Optionally, the spoiling means comprises a device for tripping electrical contacts to prevent their continued use.

Optionally the spoiling means comprises elements that cause a physical change if a particular blade portion has already been attached to the body portion previously.

Alternatively, the spoiling means comprises locking elements that break off when the blade and body are separated.

Preferably the locking elements comprise a male protrusion and a female ingression, one of which is provided on the blade and one of which is provided on the body.

Preferably the male protrusion is provided with a weakened section.

Preferably the female ingression is provided with a weakened section.

In order to provide a better understanding of the present invention, embodiments will now be described by way of example only, and with reference to the following Figures, in which.

Figure 1:
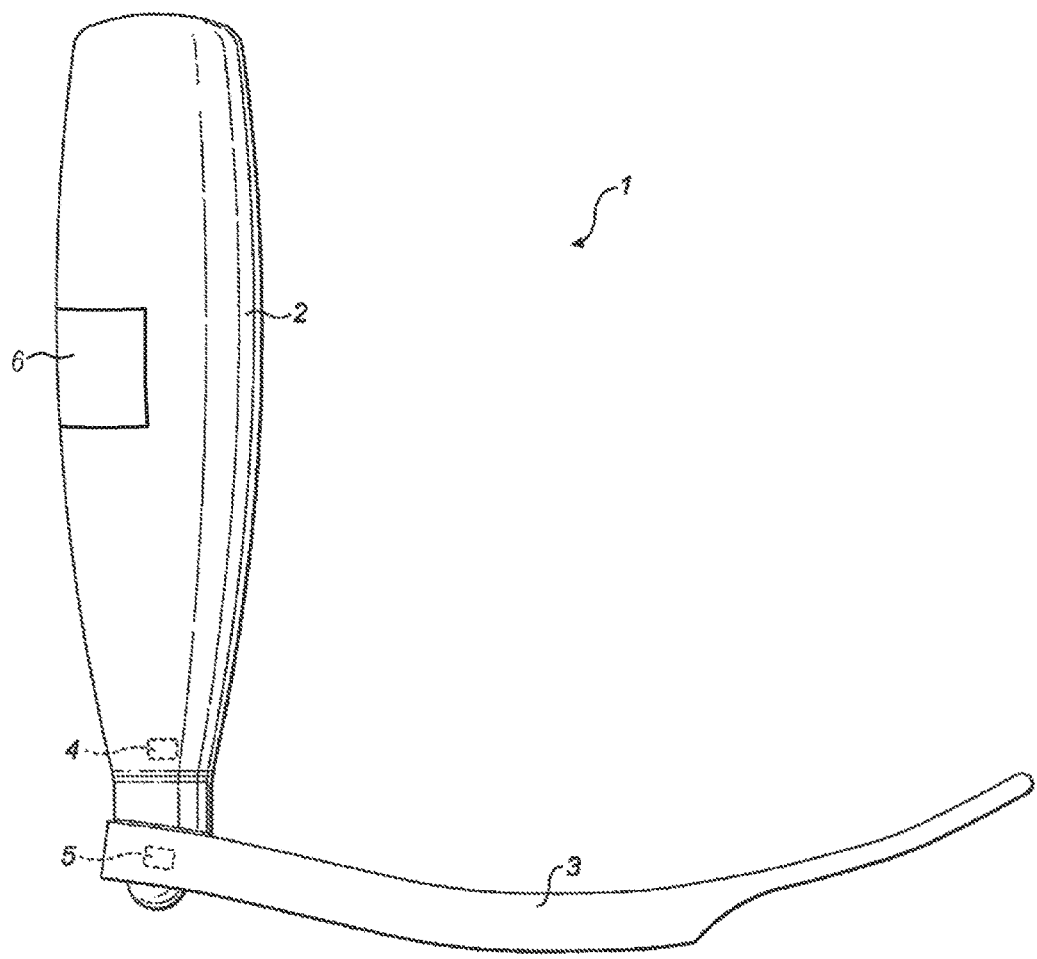
FIG. 1 shows a cross section view of a laryngoscope according to a first aspect of the present invention.
Figure 2:
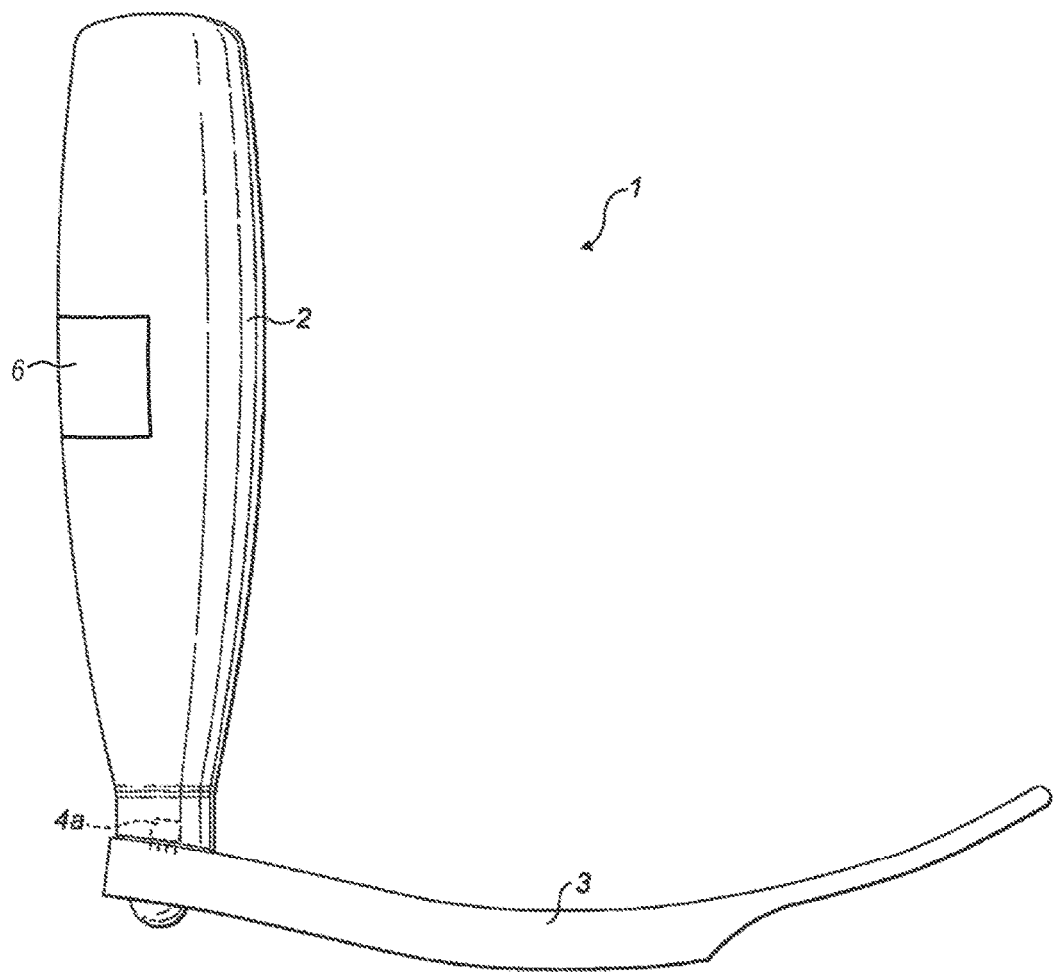
FIG. 2 shows a cross section view of a laryngoscope according to a second aspect of the present invention.

In the preferred embodiment of the present invention, the medical device is a laryngoscope that can be used for intubation of a tracheal tube.

According to the present invention, there is provided a laryngoscope 1 which has a disposable blade 3. The blade 3 is the section that comes into contact with the patient during examination. Therefore, after use the blade 3 can be disposed of and the remaining parts of the laryngoscope 1 re-used.

One of the benefits of the disposability of the blade 3 is that there will be no cross-contamination to patients, and no lengthy cleaning procedures are required. However, to ensure that a blade 3 is not reused, a spoiling mechanism is incorporated into the laryngoscope laryngoscope 1.

In one embodiment, a mother chip 4 is provided in the body 2 of the laryngoscope 1. A corresponding radio frequency tag 5 that can be recognised by the mother chip 4 is provided in the disposable blade 3. The radio frequency tag 5 is provided with a serial number and each radio frequency tag 5 has a unique serial number. When the radio frequency tag 5 and the mother chip 4 are brought into close contact i.e. by the blade 3 being attached to the body section 2, the mother chip 4 can read the serial number. If the mother chip recognises the serial number from a previous occasion this will be indicated to the user.

Alternatively, the radio frequency tag does not have a serial number, but the mother chip electronically marks the radio frequency tag, so that it can be recognised as having previously being in contact with another body. This is the preferred embodiment.

In the preferred embodiment, the body 2 is provided with a monitor 6. If the mother chip 4 recognises a serial number, or any other electronic signal on a radio frequency tag 5 of a blade that is being attached, a computer program will be in place to display a message on a monitor which is attached to the body 2 informing the user. The mother chip 4 will typically be able to both read the blade chip and write on it. This would allow a blade chip to be electronically written on in a manner that means it would be recognised by any body section that it is attached to. This is the preferred embodiment as it ensures that in emergencies for example when a paramedic is called to a scene with a significant number of casualties, a blade 3 can be re-used if absolutely necessary. It would also allow the storage of the date, time, patient details and other information, if required. An alternative to the radio frequency messaging described above would be to use a mother chip 4a that is an optical reader. There would be a mechanism for physically marking a blade 3 that has previously been used, and this physical mark would be recognised by the mother chip 4a. The physical Marks may be surface scoring, discolouring, exposure to light or faint fracture points/lines designed to appear after pressure has been applied during use.

The benefit of the abovementioned options is that the mother chip 4 or 4a could be programmed to allow a certain number of re-uses which may be within a defined period, or allow a manual override in emergency situations.

Alternatively, the spoiling mechanism can take the form of a breaking of electrical connections when the blade 3 and body 2 are parted, such that if the same blade 3 and body 2 are reconnected, no power is provided to anything inserted into the core 6 of the blade 3. A further alternative is that the blade 3 may comprise protrusions which are able to fix into ingressions in the body 2 of the laryngoscope 1, such that the protrusions break off when the blade 3 is removed from the body 2, such that the blade 3 cannot then be reused. These alternatives may be more useful in non-emergency areas such as operating theatres for routine surgery where the need to re-use a blade 3 in extreme circumstances is less likely to occur.

It can be seen that the current invention has a number of benefits over the prior art and a number of possible uses. Although the examples above relate to a laryngoscope, it can be seen that the concept can be extended to other medical and veterinary devices and still stay within the scope of the present invention. The fact that the blade is fully disposable is of great importance, as it means that practitioners are required to change blades and the product is both simple to use and cheap to manufacture.

It will be appreciated by persons skilled in the art that the above embodiment has been described by way of example only, and not in any limiting sense, and that various alterations and modifications are possible without departure from the scope of the invention as defined by the appended Claims.

The invention claimed is:

1. A laryngoscope comprising:
a body portion comprising a chip disposed on a first body end;
a blade portion separate from the body portion and comprising a first blade end and a second blade end, wherein the first blade end is configured to be removably coupled to the first body end, and wherein the chip comprises a radio frequency transmitter and a radio frequency receiver configured to send and receive signals, respectively, with a tag comprising a radio frequency receiver and a radio frequency transmitter in the blade portion and storing identification information for the blade portion, wherein the chip in the body portion, when brought into close proximity of the blade portion, is configured to read the identification information from the tag and determine if the blade has been previously brought into close proximity of the body portion, and wherein the chip is programmed to allow a certain number of re-uses of the blade portion; and
a monitor disposed on the body portion and configured to display the identification information read by the chip to inform a user of a use status of the blade portion.

2. A laryngoscope as in claim 1, wherein the radio frequency receiver in the body portion is adapted to count the number of blades the body portion comes into close proximity with.

3. A laryngoscope as in claim 1, wherein the chip comprises a device for tripping electrical contacts to prevent their continued use.

4. A laryngoscope as in claim 1, wherein the tag includes a serial number, and wherein the chip is programmed to read the serial number.

5. A laryngoscope as in claim 1, wherein the chip is programmed to electronically mark the tag on the blade portion such that the blade portion is recognized as having previously been in contact with the body portion.

6. The laryngoscope of claim 1, wherein the identification information comprises a date, time, patient information, and information associated with the use status of the blade portion.

7. A laryngoscope comprising:
a body portion, comprising a chip, the chip including a first receiver and a first transmitter, and
a blade portion, comprising a tag including a second receiver and a second transmitter,
wherein the first receiver and first transmitter in the chip are operable to send and receive signals respectively with the second transmitter and the second receiver in the tag,
wherein the blade portion is separable from the body portion, and
wherein the chip, when brought into close proximity of the blade portion, is configured to read identification information stored in the tag and to provide an output to indicate if the blade portion has been previously brought into close proximity of the body portion, and
wherein the chip is programmed to determine from the first receiver and the second transmitter if the blade has been previously brought into close proximity of the body portion and to allow a certain number of re-uses of the blade portion on a patient that is different from a patient that previously used the blade portion.

8. A laryngoscope according to claim 7, wherein the chip is programmed to allow a manual override once the blade portion is connected to the body portion.

9. The laryngoscope of claim 7, comprising a monitor disposed on the body portion and configured to display the identification information and inform a user of the laryngoscope a use status of the blade portion.

\* \* \* \* \*